(12) United States Patent
Vetter et al.

(10) Patent No.: US 10,543,135 B2
(45) Date of Patent: Jan. 28, 2020

(54) LOW MIGRATION INK COMPOSITION

(71) Applicant: The Procter & Gamble Company, Cincinnati, OH (US)

(72) Inventors: Nicholas David Vetter, Cleves, OH (US); Alrick Vincent Warner, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/002,309

(22) Filed: Jun. 7, 2018

(65) Prior Publication Data

US 2019/0002715 A1    Jan. 3, 2019

Related U.S. Application Data

(60) Provisional application No. 62/526,502, filed on Jun. 29, 2017.

(51) Int. Cl.

| | | |
|---|---|---|
| C08F 2/46 | (2006.01) | |
| C08F 2/50 | (2006.01) | |
| C08G 61/04 | (2006.01) | |
| A61F 13/84 | (2006.01) | |
| C09D 11/033 | (2014.01) | |
| A61F 13/514 | (2006.01) | |
| C09D 11/101 | (2014.01) | |
| C09D 11/037 | (2014.01) | |
| A61F 13/513 | (2006.01) | |
| B33Y 80/00 | (2015.01) | |
| A61L 15/24 | (2006.01) | |
| B33Y 70/00 | (2015.01) | |

(52) U.S. Cl.
CPC .... *A61F 13/8405* (2013.01); *A61F 13/51394* (2013.01); *A61F 13/51496* (2013.01); *A61L 15/24* (2013.01); *B33Y 70/00* (2014.12); *B33Y 80/00* (2014.12); *C09D 11/033* (2013.01); *C09D 11/037* (2013.01); *C09D 11/101* (2013.01); *A61F 2013/8497* (2013.01)

(58) Field of Classification Search
CPC ... C09D 11/106; C09D 11/037; C09D 11/033; C09D 11/101; A61L 15/00; A61F 2013/15243; A61F 13/15203; A61F 13/51394; A61F 13/8405; A61F 2013/8797; A61F 13/51496
USPC .................. 522/7, 6, 71, 189, 184, 1; 520/1
See application file for complete search history.

(56) References Cited

U.S. PATENT DOCUMENTS

| | | |
|---|---|---|
| 3,848,594 A | 11/1974 | Buell |
| 3,860,003 A | 1/1975 | Buell |
| 4,662,875 A | 5/1987 | Hirotsu et al. |
| 4,699,622 A | 10/1987 | Toussant et al. |
| 4,846,815 A | 7/1989 | Scripps |
| 4,894,060 A | 1/1990 | Nestegard |
| 4,946,527 A | 8/1990 | Battrell |
| 4,963,140 A | 10/1990 | Robertson et al. |
| 5,151,092 A | 2/1992 | Buell et al. |
| 5,221,274 A | 6/1993 | Buell et al. |
| 5,242,436 A | 9/1993 | Weil et al. |
| 5,499,978 A | 3/1996 | Buell et al. |
| 5,507,736 A | 4/1996 | Clear et al. |
| 5,554,145 A | 9/1996 | Roe et al. |
| 5,569,234 A | 10/1996 | Buell et al. |
| 5,580,411 A | 12/1996 | Nease et al. |
| 5,591,152 A | 1/1997 | Buell et al. |
| 5,628,097 A | 5/1997 | Benson et al. |
| 5,700,254 A | 12/1997 | McDowall et al. |
| 6,004,306 A | 12/1999 | Robles et al. |
| 6,120,487 A | 9/2000 | Ashton |
| 6,432,098 B1 | 8/2002 | Kline et al. |
| 6,458,335 B1 * | 10/2002 | Lemaitre .................... B01J 2/00 423/419.1 |
| 6,550,905 B1 | 4/2003 | Deckers |
| 6,645,190 B1 | 11/2003 | Olson et al. |
| 6,761,711 B1 | 7/2004 | Fletcher et al. |
| 6,817,994 B2 | 11/2004 | Popp et al. |
| 6,840,928 B2 | 1/2005 | Datta et al. |
| 6,849,067 B2 | 2/2005 | Fletcher et al. |
| 6,893,426 B1 | 5/2005 | Popp et al. |
| 6,953,452 B2 | 10/2005 | Popp et al. |
| 6,969,377 B2 | 11/2005 | Koele et al. |

(Continued)

FOREIGN PATENT DOCUMENTS

| | | | |
|---|---|---|---|
| CN | 103642318 | * | 5/2015 |
| EP | 3000853 A1 | | 3/2016 |

(Continued)

OTHER PUBLICATIONS

He et al, CN 103642318 Machine Translation, May 27, 2015 (Year: 2015).*

*Primary Examiner* — Jessica Whiteley

(74) *Attorney, Agent, or Firm* — Wednesday G. Shipp; Andrew J. Hagerty

(57) ABSTRACT

A low migration energy curable ink composition may include, based upon total composition weight: a) from about 10% to about 80% of a solvent system comprising the following: i) from about 35% to about 80% of one or more mono-functional acrylate monomers, ii) from about 10% to about 35% of one or more di-functional acrylate monomers, and iii) from about 10% to about 30% of one or more tri-functional or greater acrylate monomers; b) from about 3% to about 30% of an acrylate oligomer, and c) from about 1% to about 15% of a colorant. The low migration energy curable ink may be incorporated into an absorbent article.

17 Claims, 4 Drawing Sheets

(56) References Cited

U.S. PATENT DOCUMENTS

| | | |
|---|---|---|
| 7,156,833 B2 | 1/2007 | Couture-Dorschner et al. |
| 7,201,744 B2 | 4/2007 | Van Gompel et al. |
| 7,497,851 B2 | 3/2009 | Koele et al. |
| 7,682,349 B2 | 3/2010 | Popp et al. |
| 7,862,550 B2 | 1/2011 | Koele et al. |
| 7,893,127 B2 | 2/2011 | Nagvekar et al. |
| 7,901,393 B2 | 3/2011 | Matsuda et al. |
| 8,007,485 B2 | 8/2011 | Popp et al. |
| 8,361,048 B2 | 1/2013 | Kuen et al. |
| 8,372,052 B2 | 2/2013 | Popp et al. |
| 8,579,876 B2 | 11/2013 | Popp et al. |
| 8,747,379 B2 | 6/2014 | Fletcher et al. |
| 8,771,787 B2 | 7/2014 | Breton et al. |
| 9,421,137 B2 | 8/2016 | Lavon et al. |
| 2011/0157682 A1* | 6/2011 | Zang .................... C08G 18/672 359/296 |
| 2012/0330262 A1 | 12/2012 | Lawson et al. |
| 2014/0005020 A1 | 1/2014 | LaVon et al. |
| 2015/0088088 A1 | 3/2015 | Wade et al. |
| 2015/0126955 A1 | 5/2015 | Sauer et al. |
| 2015/0344722 A1 | 12/2015 | Lin |
| 2016/0020648 A1 | 1/2016 | Contopanagos |
| 2016/0136014 A1 | 5/2016 | Arora et al. |
| 2016/0270972 A1 | 9/2016 | Surushe et al. |

FOREIGN PATENT DOCUMENTS

| | | | |
|---|---|---|---|
| IN | 270327 | 12/2015 | |
| WO | WO2014028203 A1 | 2/2014 | |
| WO | WO-2014030015 A1 * | 2/2014 | ........... C09D 11/101 |
| WO | WO2014184548 A1 | 11/2014 | |
| WO | WO2016096632 A1 | 6/2016 | |

\* cited by examiner

LOW MIGRATION INK COMPOSITION

FIELD OF THE INVENTION

The invention relates to energy curable inks, especially energy curable inks having low migration and low migration component materials, and absorbent articles comprising said inks.

BACKGROUND OF THE INVENTION

The printing of substrates, such as woven and nonwoven fabrics and films, is well known. Many current products, such as diapers and training pants, include printed designs to improve their appearance. Energy curable inks provide many desirable properties including enhanced visual appeal and the ability to digitally print such articles. However, without sufficient adhesion and curing, the printed design can be smeared or even be removed during manufacturing and packaging, especially when printing and manufacturing at high speeds. Further, rub-off, smearing or other form of ink release may occur during product handling and use. As such, the lack of curing and/or adhesion undermines the desired print quality and could even cause skin irritation for the end user. Indeed, manufacturers have struggled to balance high print quality with reduced smudging and reduced skin irritation. Thus, there remains a need to formulate ink compositions that will cure efficiently and to high degree. There is also a need for ink compositions that avoid skin irritation. In addition, there is a need for a printed substrate having improved print quality, improved ink adhesion, reduced ink rub-off, improved vibrancy, low ink migration and/or low ink component migration, while still delivering a high level of ink curing, especially where said printed substrate may be used in an absorbent article.

SUMMARY OF THE INVENTION

The present invention relates to a low migration energy curable ink composition having, based on total composition weight, from about 10% to about 80% of a solvent system comprising acrylate monomers, from about 3% to about 30% of an acrylate oligomer, and from about 1% to about 15% of a pigment. The solvent system may include from about 35% to about 80% of one or more mono-functional acrylate monomers, from about 10% to about 35% of one or more di-functional acrylate monomers; and from about 10% to about 30% of one or more tri-functional or greater acrylate monomers. The solvent system may consist essentially of low migratory components. The low migration energy curable ink may be applied to a substrate which is incorporated into an absorbent article.

DETAILED DESCRIPTION OF THE INVENTION

Definitions

Figure 1:
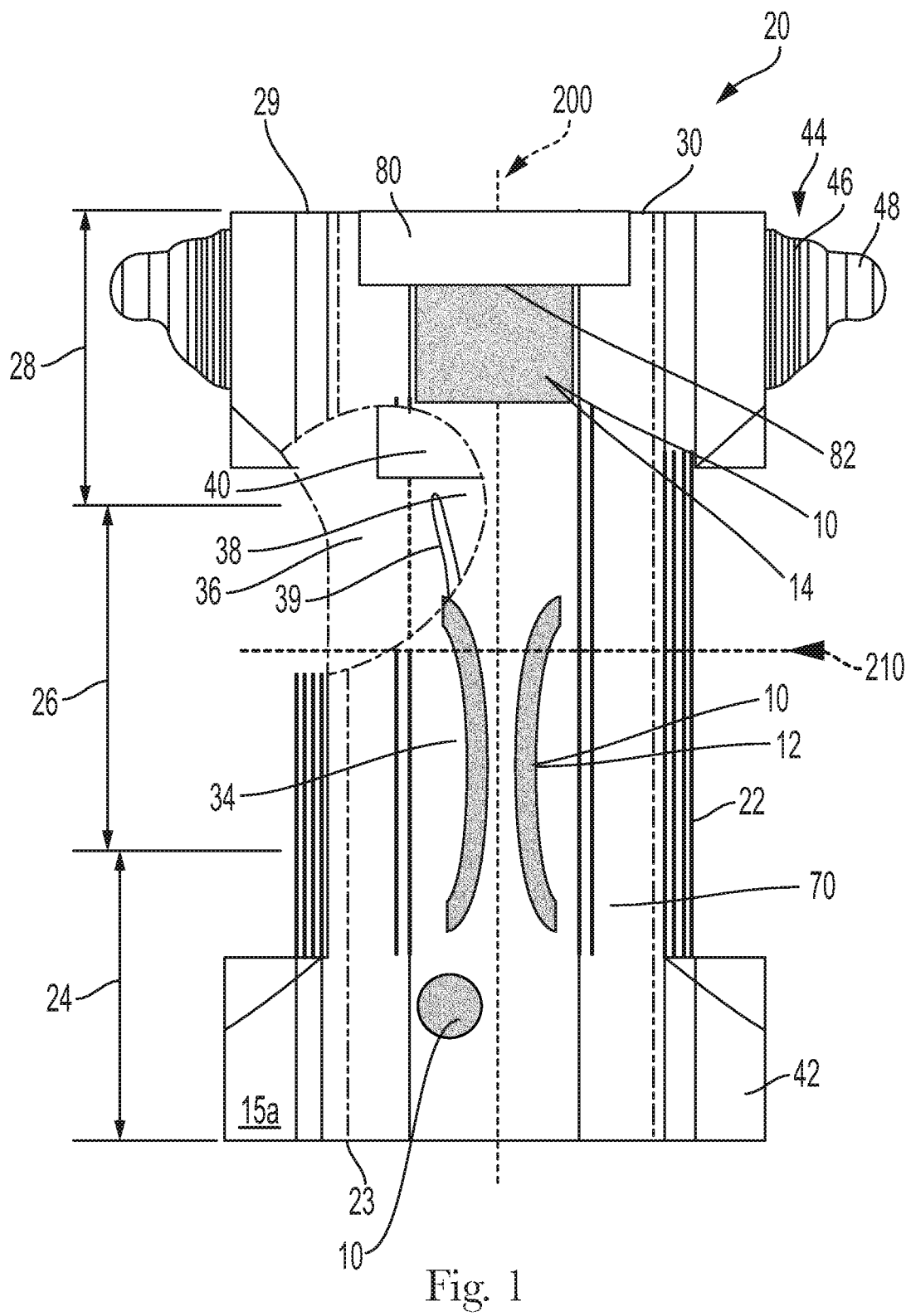
FIG. 1 is a schematic plan view of an exemplary embodiment of an absorbent article as detailed herein. The absorbent article is shown in a flat, uncontracted state.

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Colorant" includes one or more of pigments and or dyes; colorant may further include an acrylic colloidal dispersion, acrylic solution, or surfactants and water.

"Color Density" and "Optical Density," otherwise referred to as "ink density", is a function of the percentage of light reflected from a printed patch of printed ink. Ink Density is a unitless value correlating to the vibrancy of the ink printed onto a substrate. A low percentage of light reflected results in a high density. Data derived herein is based on an X-rite eXact Spectrophotometer for measurements.

"Design element" as used herein means a shape or combination of shapes that visually create a distinct and discrete component, regardless of the size or orientation of the component. A design element may be present in one or more patterns. A design element may be present one or more times within one pattern. In a nonlimiting example, the same design element is present twice in one pattern—the second instance of the design element is smaller than the first instance. One of skill in the art will recognize that alternative arrangements are also possible. Design elements may comprise insignia. Design elements and/or combinations of design elements may comprise letters, words and/or graphics such as flowers, butterflies, hearts, character representations and the like. Design elements and/or combinations of design elements may comprise instructional indicia providing guidance or instruction to the caregiver relative to placement and/or fit of the article about the wearer.

"Film" means a sheet-like material wherein the length and width of the material far exceed the thickness of the material (e.g., 10×, 50×, or even 1000× or more). Films are typically liquid impermeable but may be configured to be breathable "Functional indicia" as used herein means an indication or a signal perceptible to the user that corresponds to a functionally-distinguishable portion of a component, such as an absorbent article or subcomponents of an absorbent article.

"Insignia" as used herein means objects, character representations, words, colors, shapes or other indicia that can be used to distinguish, identify or represent the manufacturer, retailer, distributor or brand of a product, including but not limited to trademarks, logos, emblems, symbols, designs, figures, fonts, lettering, crests or similar identifying marks.

"Low migratory" in reference to a component (i.e., a component of a solvent system, of a composition, etc.) means a material listed on Annex 6 of the Swiss Ordinance on Materials and Articles in Contact with Food (RS 817.023.21), 4$^{th}$ edition, issued by the Swiss Federal Department of Health Affairs on Jan. 1, 2012, provided at the material's respective SML (specified migration limit) set by RS817.023.21.

"Nonwoven" means a porous, fibrous material made from continuous (long) filaments (fibers) and/or discontinuous (short) filaments (fibers) by processes such as, for example, spunbonding, meltblowing, airlaying, carding, coforming, hydroentangling, and the like. Nonwovens do not have a woven or knitted filament pattern. Nonwovens may be liquid permeable or impermeable.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

"Pattern" as used herein means a decorative or distinctive design, not necessarily repeating or imitative, including but not limited to the following: clustered, geometric, spotted, helical, swirl, arrayed, textured, spiral, cycle, contoured, laced, tessellated, starburst, lobed, blocks, pleated, concave, convex, braided, tapered, and combinations thereof.

"Substrate" includes any material that the inks of the present invention can be printed on. Thus, substrates of the present invention include, but are not limited to, nonwovens, films, fibrous polyolefin webs, polyolefin webs, cellulosic webs, elastomeric webs, laminates of one or more of the above or any combination of one or more of the above.

"Web" means a material capable of being wound into a roll. Webs may be films, nonwovens, laminates, apertured films and/or laminates, and the like. The face of a web refers to one of its two dimensional surfaces, as opposed to its edge.

Ink Composition

In some embodiments, a curable ink composition 10 may comprise an acrylate-based solvent system. The solvent system may be from about 10% to about 80% of the ink composition (based on the weight of the total composition), reciting for said range every 5% increment therein. The solvent system may comprises acrylate monomers, including mono-functional acrylate monomers and multifunctional acrylate monomers (i.e., di-functional acrylates, tri-functional acrylates, tetra-functional acrylates, etc.). The solvent system may comprise from about 35% to about 80% of one or more mono-functional acrylates by weight of the solvent system, reciting for said range every 5% increment therein. Additionally or alternatively, the solvent system may comprise from about 10% to about 35% of one or more di-functional acrylate and/or from about 10% to about 30% of one or more tri-functional or greater acrylates by weight of the solvent system reciting for each range every 5% increment therein. The acrylate-based solvent system is curable by exposure to energy, undergoing crosslinking reactions. In this way, the solvent system does not evaporate and the ink does not dry as with traditional solvent based inks.

Suitable mono-functional acrylate monomers for the solvent system include octyl acrylate, decyl acrylate, isodecyl acrylate, isodecyl methacrylate, tridecyl acrylate, dimethylaminoethyl methacrylate, 2-phenoxyethyl acrylate, isobornyl acrylate, 2(2-ethoxyethoxy)ethyl acrylate, nonylphenol acrylate, ethoxylated nonylphenol acrylate, stearyl acrylate, tetrahydrofurfuryl acrylate, aliphatic acrylate, caprolactone acrylate, lauryl acrylate, cyclic trimethylolpropane formal acrylate, and combinations thereof. In some embodiments, the one or more mono-functional acrylates comprise low migratory mono-functional acrylates.

Suitable di-functional acrylate monomers for the solvent system include tricyclodecane dimethanol diacrylate, tripropylene glycol diacrylate, tripropylene glycol dimethacrylate, dipropylene glycol diacrylate, dipropylene glycol dimethacrylate, cyclohexanedimethanol diacrylate, 1,6-hexanediol diacrylate, 1,6-hexanediol dimethacrylate, ethoxylated hexanediol diacrylate, propoxylated hexanediol diacrylate, 1,3-butanediol diacrylate, 1,4-butanediol diacrylate, neopentyl glycol diacrylate, propoxylated neopentyl glycol diacrylate, diethylene glycol diacrylate, diethylene glycol dimethacrylate, triethylene glycol diacrylate, triethylene glycol dimethacrylate, tetraethylene glycol diacrylate, tetraethylene glycol dimethacrylate, polyethylene glycol-200-diacrylate, 3-ethoxylated bisphenol-A diacrylate, and combinations thereof. In some embodiments, the one or more di-functional acrylates comprise low migratory di-functional acrylates.

Suitable tri-functional or greater acrylate monomers include trimethylol propane triacrylate, trimethylol propane trimethacrylate, ethoxylated trimethylol propane triacrylate, 6-ethoxylated trimethylol propane triacrylate, 9-ethoxylated trimethylol propane triacrylate, 15-ethoxylated trimethylol propane triacrylate, 20-ethoxylated trimethylol propane triacrylate, propoxylated trimethylol triacrylate, propoxylated glyceryl triacrylate, pentaerythritol triacrylate, pentaerythritol tetraacrylate, di-trimethylol propane tetraacrylate, di-pentaerythritol pentaacrylate, di-pentaerythritol hexaacrylate, and combinations thereof In some embodiments, the one or more tri-functional or greater acrylates comprise low migratory acrylates that are tri-functional or greater (e.g., tetra-functional).

In embodiments, the solvent system comprises one or more mono-functional acrylates selected 5from the group lauryl acrylate, 2(2-ethoxyethoxy)ethyl acrylate, 2-phenoxyethyl acrylate, isobornyl acrylate, isodecyl methacrylate, tetrahydrofufuryl acrylate, or dimethylaminoethyl methacrylate, and combinations thereof; and/or one or more di-functional acrylates selected from the group of dipropylene glycol diacrylate, tripropylene glycol diacrylate, ethoxylated hexanediol diacrylate, propoxylated hexanediol diacrylate, and combinations thereof; and/or one or more tri-functional or greater level functional acrylates selected from the group of trimethylol propane triacrylate, alkoxylated trimethylolpropane triacrylate, trimethylol propane trimethacrylate, alkoxylated glyceryl triacrylate, and combinations thereof.

Additionally or alternatively, the solvent system may consist essentially of or consist of low migratory acrylate monomers. Further, the solvent system may comprise a Functional Ratio of, based on weight of the solvent system, of at least about 2, or from about 3 to about 12, or from about 5 to about 10, or from about 7 to about 9.5, or from about 8.5:1 to about 9.2:1, or from about 2 to 7 reciting for each range every 1 increment therein, wherein the Functional Ratio is the weight ratio as monomers as shown in the formula below:

$$\text{Functional Ratio} = \frac{\text{monofunctional monomers} + \text{difunctional monomers}}{\text{trifunctional and higher monomers}}$$

The ink composition 10 may further comprise from about 3% to about 30% of one or more acrylate oligomers, based on the weight of the composition, reciting for said range every 3% increment therein. Suitable acrylate oligomers include epoxy acrylate oligomer, a polyester acrylate oligomer, a urethane acrylate oligomer, an aliphatic urethane acrylate oligomer, an aromatic urethane acrylate oligomer, an aliphatic acrylate oligomer, or an acrylic oligomer, and combinations thereof. The acrylate oligomer may comprise at least 2 functional groups, or 12 or less functional groups, or 6 or less than functional groups, or about 4 or less functional groups, or from about 2 to about 6 functional groups, reciting for said range every 1 increment therein. In nonlimiting examples, oligomer(s) may comprise a glass transition temperature of 50° C. or less. In some embodiments, the one or more oligomers comprises a low migratory acrylate oligomer. The one or more oligomers may consist essentially of or consist of low migratory acrylate oligomers.

The ink composition 10 may further comprise photoinitiators, in particular two or more photoinitiators. In embodiments, the composition 10 may comprise from about 3% to about 15% of photoinitiators, or from about 3% to about 15% of two or more photoinitiators, based on the weight of the composition, reciting for each range every 1% increment therein. The photoinitiators may be selected from a Norrish Type I or Norrish Type II photoinitiator. The photoinitiators may be selected from the group of alpha hydroxyl ketones, alpha amino ketones, acyl phosphine oxides, benzyldimethyl ketals, benzophenones, thioxanthones, and combinations thereof. In nonlimiting examples, the photoinitiators include:

alpha hydroxyl ketones selected from the group consisting of: 2-hydroxy-4'-(2-hydroxyethoxy)-2-methylpropiophenone, 1-hydroxycyclohexyl-phenyl-ketone, 2-hydroxy-2-methylpropiophenone; oligo[2-hydroxy-2-methyl-1-[4-(1-methylvinyl)phenyl]propanone]; 1-[4-(2-Hydroxyethoxy)-phenyl]-2-hydroxy-2-methyl-1-propanone; 1-[4-[(4-benzoylphenyl)thio]phenyl]-2-methyl-2-[(4-methylphenyl)sulfonyl]-1-propanone; and mixtures thereof;

alpha amino ketones are selected from the group consisting of: -methyl-1-[4-(methylthio)phenyl]-2-morpholinopropan-1-one, 2-benzyl-2-dimethylamino-4'-morpholinobutyrophenone, bis(p-(N,N-dimethylamino)phenyl)ketone; and mixtures thereof, and/or acyl phosphine oxides are selected from the group: 2bis (2,4,6-trimethylbenzoyl)-phenylphosphine oxide, 2,4,6-trimethylbenzoyldiphenyl phosphine oxide, 2,4,6-trimethylbenzoyl phosphine oxide; ethyl-(2,4,6-trimethylbenzoyl)phenylphosphinate; a 20/80 blend of phenyl bis(2,4,6-trimethyl benzoyl)phosphine oxide and a phosphine oxide derivatives; and mixtures thereof.

In further nonlimiting examples, the photoinitiators may be selected from the group of 2-methyl-1-[4-(methylthio) phenyl]-2-morpholinopropan-1-one, bis(2,4,6-trimethylbenzoyl)-phenylphosphine oxide, 2-hydroxy-2-methylpropiophenone, 2-hydroxy-4'-(2-hydroxyethoxy)-2-methylpropiophenone, 1-hydroxycyclohexyl-phenyl-ketone, 2,2-dimethoxy-1,2-diphenylethan-1-one, 2,4,6-trimethylbenzoyldiphenyl phosphine oxide, 2-benzyl-2-dimethylamino-4'-morpholinobutyrophenone, and mixtures thereof. In some embodiments, a photoinitiator may comprises a low migratory photoinitiator.

In alternative embodiments, the composition may be void of photoinitiators.

The ink composition 10 can also include a colorant. In some embodiments, the ink comprises cyan, magenta, yellow, black or combinations thereof. In some embodiment, the composition may comprise 1% to about 15% of a colorant, based on the weight of the composition. The colorant may be in the form of one or more pigments. Nonlimiting examples of colorants include those having the following COLOR INDEX™ classifications: Green PG 7 and 36; Orange PO 5, 16, 34, 36, 38, 43, 51, 60, 62, 64, 66, 67 and 73; Red PR 101, 112, 122, 146, 149, 170, 176, 178, 179, 181, 185, 187, 188, 200, 202, 207, 208, 214, 220, 224, 242, 251, 254, 255, 260, 264, 48:1, 48:2, 48:3, 52, 52:1, and 57:1; Magenta/Violet PV 19, 23, 31, and 37; Yellow PY 12, 13, 14, 17, 74, 83, 120, 138, 139, 155, 151, 168, 175, 179, 180, 181 and 185; Blue PB 15, 15:1, 15:2, 15:3, 15:4, 15:6; Black PB 2, 5 and 7; carbon black; titanium dioxide (including rutile and anatase); zinc sulfide, and combinations thereof. COLOR INDEX™ classifications are published by the Association of Textile Chemists and Colorists and the Society of Dyers and Colourists. One or more pigments may be low migratory pigments.

A pigment may be provided in the form of a dispersion. Further, the pigment may have an average particle size of about 1000 nm or less, or about 800 nm or less.

The ink composition may comprise one or more additives. In certain embodiments, the composition comprises from about 0.5% to about 5% of one or more additives, based on weight of the ink composition (reciting for said range every 0.5% increment therein). The additives may include antioxidants, stabilizers, anti-misting agents, optical brighteners, surfactants, slip agents, waxes, silicones, defoamers, flow agents and leveling agents, solvents, amine curing synergists, gloss enhancers, rheology modifiers and combinations thereof, or any other suitable ink additive known in the art.

The ink composition 10 may consist essentially of low migratory components, such as low migratory acrylate monomers, low migratory oligomers, low migratory photoinitiators and/or low migratory pigments. In some embodiments, excluding additives, the ink composition consists of low migratory components. In some embodiments, the ink composition comprising acrylate monomers, oligomers, and photoinitiators may be mixed together and incorporate to form a low migratory ink composition. In certain embodiments, the ink composition comprises 2% or less of water, based on the weight of the composition.

The ink composition may have a surface tension of 15 dyne/cm² to about 40 dyne/cm², reciting for said range every 5 dyne/cm² increment therein. The ink composition may have a viscosity ranging from about 5 cps to about 40 cps at 25° C., reciting for said range every 5 cps increment therein.

The curable ink composition 10 may be applied to a substrate 15. The substrate may comprise a polyolefin material. The substrate 15 may comprise a nonwoven, a film, or a laminate of nonwovens and/or films. In some embodiments, the substrate may be provided with an attachment portion, such as an adhesive attachment portion, allowing the substrate to be attached to another component. In nonlimiting examples, the substrate may be a paper having an adhesive backing or other label constructions known in the art.

The ink may be applied in one or more design elements 12, including but not limited to graphics, letters, instructional indicia, functional indicia and insignia. In some embodiments, the ink is disposed in a pattern 14, as shown for example in FIG. 1 where one printed portion is shown to comprise a pattern 14. In some nonlimiting examples, the ink is disposed in functional indicia as illustrated for example in FIG. 1 wherein the curved design elements may signal the presence of channels 39. In further nonlimiting examples, the ink may be disposed in instructional indicia, such as the size of an article, fit instructions, use instructions or other instructions.

In some embodiments, the ink composition 10 is applied with an ink jet printer as is known in the art. In further embodiments, the ink composition is cured by applying ultraviolet light, LED and/or e-beam. In further embodiments, the ink composition 10 may comprise an ultraviolet curable ink (i.e., an UV curable ink). UV curable inks are cured by exposure to ultraviolet waves, typically in the range of from about 200 nm to about 400 nm, or from about 300 nm to about 400 nm, reciting for each range every 10 nm increment therein. UV inks incorporate one or more photoinitiators to trigger the crosslinking polymerization. The type of photoinitiator may affect the wavelength necessary for curing. UV inks may be cured using energy dosage of at least about 10 mJ/cm$^2$, or about 2000 mJ/cm$^2$ or less, or about 1000 mJ/cm$^2$ or less, from about 10 mJ/cm$^2$ to about 2000 mJ/cm$^2$, or from about 25 mJ/cm$^2$ to about 1000 mJ/cm$^{2t}$ reciting for each range every 10 mJ/cm$^2$ increment therein. In further nonlimiting examples, LED lamps may be used during the curing process. Without being bound by theory, it is believed different levels of energy and/or different wavelengths may be used depending on conditions such as curing time, substrate type (i.e., nonwoven or other substrate), ink composition, and/or amount of ink.

In certain embodiments, the ink composition is cured by electron irradiation (i.e., e-beam ink) at a dosage suitable to result in curing the ink to the substrate. Nonlimiting examples of suitable doses of electron irradiation experienced by the substrate and ink include from about 0.5 MRads to about 10 MRads, or from about 1 MRad to about 5 MRads, reciting for each range every 1 increment therein. Nitrogen gas ($N_2$) may be used to facilitate the curing process to ensure maximal energy is directed to the ink. Without being bound by theory, it is believed different levels of electron irradiation may be used depending on parameters such as curing time, substrate type (e.g., nonwoven or other substrate), ink composition, and/or amount of ink.

The ink on the substrate may have an optical density of 0.2 or greater, or 0.4 or greater, or 0.7 or less, or from about 0.4 to about 0.6 according to the Method for Measuring Color Density herein. The ink on the substrate may have an Ink Adhesion Rating of at least 2, or at least 2.5, or from about 2 to about 5, or from about 2.5 to about 4, or about 4, reciting for each range every 0.5 increment therein, according to the Ink Rub-Off Test Method herein.

In some embodiments, the ink composition comprises a Migration Rating of about 1.0 or greater, about 1.04 or greater, or about 1.06 or greater, or about 1.2 or less, or about 1.15 or less, from about 1.0 to about 1.15, reciting for said range every 0.01 increment therein, according to the Migration Test Method herein.

Absorbent Article

An ink 10 according the present invention may be utilized in various articles, including absorbent articles 20. In some embodiments, the ink composition 10 is disposed on one or more substrates 15 within an absorbent article 20. By way of nonlimiting example, the ink composition 10 may be applied to the topsheet, backsheet, acquisition distribution system, ears and/or fasteners, each of which is discussed in more detail below. The ink composition may be applied to a body-facing side 15a of a substrate (see FIG. 1) and/or the ink composition may be applied to a garment-facing side 15b of a substrate (see FIG. 4). Additionally or alternatively, the ink may be visible through the body-facing side of the article 20 and/or visible through the garment-facing side of the article 20. Where ink is disposed on multiple substrates 15, the substrates may comprise the same or different amounts of ink, design elements, ink adhesion ratings, optical densities, migration ratings, and combination thereof.

FIG. 1 is a plan view of an exemplary, non-limiting embodiment of an absorbent article 20 of the present invention in a flat, uncontracted state. The body-facing surface of the absorbent article 20 is facing the viewer. The absorbent article 20 includes a longitudinal centerline 200 and a lateral centerline 210.

The absorbent article 20 comprises a chassis 30. The absorbent article 20 and chassis 30 are shown to have a first waist region 24, a second waist region 28 opposed to the first waist region 24, and a crotch region 26 located between the first waist region 24 and the second waist region 28. The waist regions 24 and 28 generally comprise those portions of the absorbent article 20 which, when worn, encircle the waist of the wearer. The waist regions 24 and 28 may include elastic members such that they gather about the waist of the wearer to provide improved fit and containment. The crotch region 26 is the portion of the absorbent article 20 which, when the absorbent article 20 is worn, is generally positioned between the legs of the wearer.

The outer periphery of the chassis 30 is defined by longitudinal edges 22 and waist edges (first waist edge 23 in first waist region 24 and second waist edge 29 in second waist region 28). The chassis 30 may have opposing longitudinal edges 22 that are oriented generally parallel to the longitudinal centerline 200. However, for better fit, longitudinal edges 22 may be curved or angled to produce, for example, an "hourglass" shape article when viewed in a plan view as shown in FIG. 1. The chassis 30 may have opposing lateral edges 23, 29 (i.e., the first waist edge 23 and second waist edge 29) that are oriented generally parallel to the lateral centerline 210.

The chassis 30 may comprise a liquid permeable topsheet 34, a backsheet 36, and an absorbent core 38 between the topsheet 34 and the backsheet 36. The topsheet 34 may be joined to the core 38 and/or the backsheet 36. The backsheet 36 may be joined to the core 38 and/or the topsheet 34. It should be recognized that other structures, elements, or substrates may be positioned between the core 38 and the topsheet 34 and/or backsheet 36. In some embodiments, an acquisition-distribution system 40 is disposed between the topsheet 36 and the absorbent core 38.

In certain embodiments, the chassis 30 comprises the main structure of the absorbent article 20 with other features added to form the composite absorbent article structure. While the topsheet 34, the backsheet 36, and the absorbent core 38 may be assembled in a variety of well-known configurations, absorbent article configurations are described generally in U.S. Pat. Nos. 3,860,003; 5,151,092; 5,221,274; 5,554,145; 5,569,234; 5,580,411; and 6,004,306.

Topsheet

The topsheet 34 is the part of the absorbent article 10 that is in contact with the wearer's skin. The topsheet 34 may be joined to portions of the backsheet 36, the absorbent core 38, the leg cuffs 70, and/or any other layers as is known to those of ordinary skill in the art. The topsheet 34 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured, may have any suitable three-dimensional features, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Publication No. US 2016/0136014 to Arora et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet. The topsheet 34 may be fully or partially elasticized or may be foreshortened so as to provide a void space between the topsheet 34 and the core 38. In nonlimiting examples, the topsheet 34 comprises the printed substrate 15.

Backsheet

The backsheet 36 is generally that portion of the absorbent article 10 positioned proximate to the garment-facing surface of the absorbent core 38. The backsheet 36 may be joined to portions of the topsheet 34, the absorbent core 38, and/or any other layers of the absorbent article by any attachment methods known to those of skill in the art. The backsheet 36 prevents, or at least inhibits, the bodily exudates absorbed and contained in the absorbent core 38 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

The backsheet 36 may also comprise more than one layer. The backsheet 36 may comprise an outer cover and an inner layer. The outer cover may be made of a soft, non-woven material. The outer cover forms at least a portion of the garment-facing surface of the absorbent article and effectively "covers" the inner layer so that film is not present on the garment-facing surface. The outer cover may comprise a bond pattern, apertures, and/or three-dimensional features. The inner layer may be made of a substantially liquid-impermeable film, such as a polymeric film. The outer cover and an inner layer may be joined together by adhesive or any other suitable material or method. In nonlimiting examples, the backsheet 36 comprises the printed substrate 15. The ink composition may be disposed on the outer cover and/or inner layer.

Absorbent Core

The absorbent core 38 is the component of the absorbent article 20 having the most absorbent capacity and that comprises an absorbent material. In some instances, absorbent material 50 may be positioned within a core bag or a core wrap 52. The absorbent material may be profiled or not profiled, depending on the specific absorbent article. The absorbent core 38 may comprise, consist essentially of, or consist of, a core wrap, absorbent material 52, and glue enclosed within the core wrap. The absorbent material may comprise superabsorbent polymers, a mixture of superabsorbent polymers and air felt, only air felt, and/or a high internal phase emulsion foam. In some instances, the absorbent material may comprise at least 80%, at least 85%, at least 90%, at least 95%, at least 99%, or up to 100% superabsorbent polymers, by weight of the absorbent material. In certain embodiments, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The absorbent core periphery, which may be the periphery of the core wrap, may define any suitable shape, such as rectangular "T," "Y," "hour-glass," or "dog-bone" shaped, for example. An absorbent core periphery having a generally "dog bone" or "hour-glass" shape may taper along its width towards the crotch region of the absorbent article.

Figure 2:
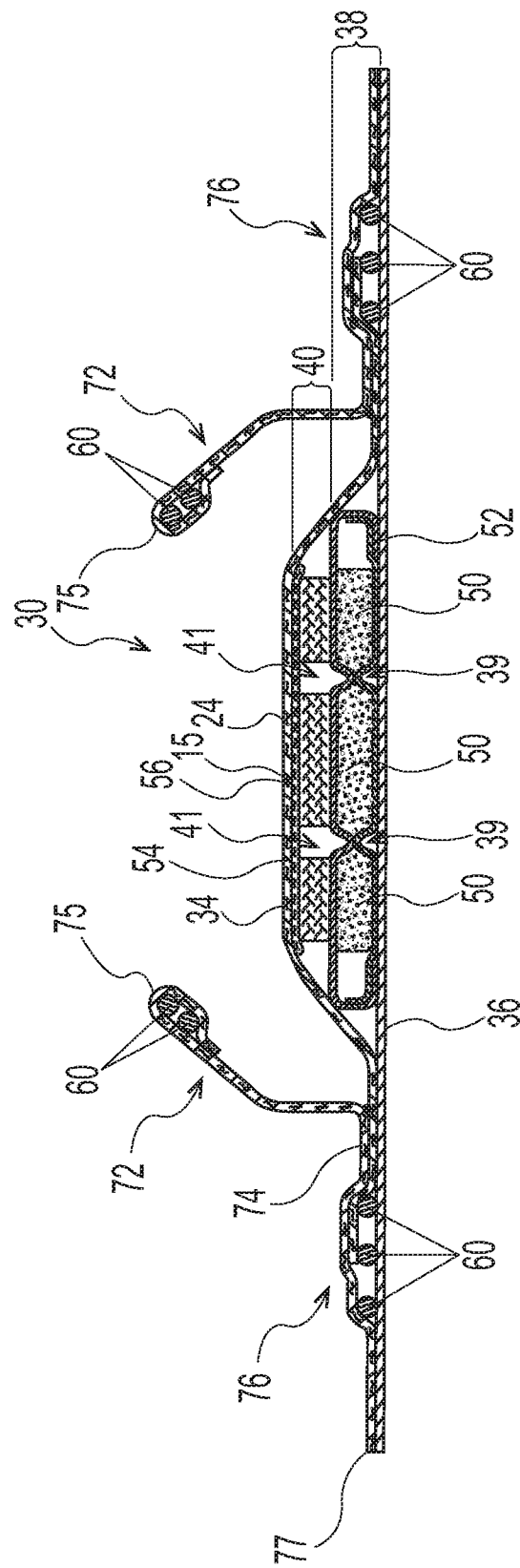
FIG. 2 is a cross-sectional view of the absorbent article taken about the lateral centerline in FIG. 1 in accordance with a non-limiting embodiment of the present invention.

Referring to FIGS. 1-2, the absorbent core 38 may have areas having little or no absorbent material 50, where a wearer-facing surface of the core bag 52 may be joined to a garment-facing surface of the core bag 52. These areas having little or no absorbent material may be referred to as "channels" 39. These channels can embody any suitable shapes and any suitable number of channels may be provided. The channels 39 may extend longitudinally or laterally. The absorbent core may further comprise two or more channels. In one nonlimiting example, two channels are symmetrically disposed about the longitudinal centerline. In other instances, the absorbent core may be embossed to create the impression of channels. The absorbent core in FIGS. 1-2 is merely an example absorbent core. Many other absorbent cores with or without channels are also within the scope of the present disclosure.

Acquisition-Distribution System (ADS)

The absorbent article may comprise an ADS 40. One function of the ADS is to quickly acquire one or more of the fluids and distribute them to the absorbent core in an efficient manner. The ADS may comprise one, two or more layers, which may form a unitary layer or may remain as discrete layers which may be attached to each other. The ADS 40 may include hydrophilic materials that provide significant wicking of bodily exudates. These materials may dewater the topsheet 34 and quickly move bodily exudates into the absorbent core 38. The ADS 40 may comprise one or more nonwoven materials, foams, cellulosic materials, cross-linked cellulosic materials, air laid cellulosic nonwoven materials, spunlace materials, or combinations thereof, for example. In some instances, portions of the ADS 40 may extend through portions of the topsheet 34, portions of the topsheet 34 may extend through portions of the ADS 40, and/or the topsheet 34 may be nested with the ADS 40. Typically, an ADS 40 may have a width and length that are smaller than the width and length of the topsheet 34. As shown in FIG. 2, the ADS may have one or more channels 41 as described above with reference to the absorbent core 38 (including the embossed version). The channels 41 in the ADS may align or not align with channels 39 in the absorbent core 30. In an example, a first acquisition material may comprise a nonwoven material and as second acquisition material may comprise a cross-linked cellulosic material. In an example, the ADS may comprise a distribution layer 54 and/or an acquisition layer 56 disposed between the absorbent core and the topsheet. Suitable ADS are described in WO 2000/59430, WO 95/10996, U.S. Pat. No. 5,700,254, and WO 02/067809, for example. In nonlimiting examples, the ADS comprises the printed substrate 15. For instance, a nonwoven material disposed in the ADS may comprise the printed substrate 15.

Ears/Fasteners

The absorbent article 20 may include front ears 42 and/or back ears 44. The ears 42, 44 may be extensible, inextensible, elastic, or inelastic. The ears 42, 44 may be formed from nonwoven webs, woven webs, knitted fabrics, polymeric and elastomeric films, apertured films, sponges, foams, scrims, and combinations and laminates thereof. In certain embodiments, the ears 42, 44 may be formed of a stretch laminate such as a nonwoven/elastomeric material. Additionally or alternatively, an ear 42, 44 may include elastic strands or other elastomers. The ears 42, 44 may be integral with the chassis, or discrete and joined to the chassis. In some embodiments, one or more ears may comprise a printed substrate 15. The ink composition may be visible from a body-facing side and/or garment-facing side of the ear.

The absorbent article 20 may also include a fastening system 46, which may be joined to an ear 44. When fastened, the fastening system 46 interconnects the first waist region 16 and the rear waist region 18 resulting in a waist circumference that may encircle the wearer during wear of the absorbent article 20. The fastening system 46 may comprise a fastener 48 such as tape tabs, hook and loop fastening components, interlocking fasteners such as tabs & slots, buckles, buttons, snaps, and/or hermaphroditic fastening components, although any other known fastening means are generally acceptable. Some exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 46 may also provide a means for holding the article in a disposal configuration as disclosed in U.S. Pat. No. 4,963,140. The fastening system 46 may also include primary and secondary fastening systems, as disclosed in U.S. Pat. No. 4,699,622. The fastening system 46 may be constructed to reduce shifting of overlapped portions or to improve fit as disclosed in U.S. Pat. Nos. 5,242,436; 5,499,978; 5,507,736; and 5,591,152. In some embodiments, the fastening system 46 and/or the fastener 48 is foldable. In certain embodiments, the fastening system 46 comprises a printed substrate 15.

Leg Gasketing System

The absorbent article 20 may comprise a leg gasketing system 70 attached to the chassis 30, which may comprise one or more cuffs. As shown in FIG. 2, the leg gasketing system may comprise a pair of barrier leg cuffs 72. Each barrier leg cuff may be formed by a piece of material which is bonded to the absorbent article so it may extend upwards from a wearer-facing surface of the absorbent article and provide improved containment of fluids and other body exudates approximately at the junction of the torso and legs of the wearer. The barrier leg cuffs are delimited by a proximal edge 74 joined directly or indirectly to the topsheet 34 and/or the backsheet 36 and a free terminal edge 75, which is intended to contact and form a seal with the wearer's skin. In some embodiments, the free terminal edge 75 comprises a folded edge as shown in FIG. 2. The barrier leg cuffs 72 extend at least partially between the front waist edge 23 and the rear waist edge 29 of the absorbent article on opposite sides of the longitudinal centerline 200 and are at least present in the crotch region. The barrier leg cuffs may be joined at the proximal edge 74 with the chassis of the article by a bond which may be made by gluing, fusion bonding, or a combination of other suitable bonding processes. The barrier leg cuffs may be integral with the topsheet 34 or the backsheet 36 or may be a separate material joined to the article's chassis. Each barrier leg cuff 72 may comprise one, two or more elastic elements 60 close to the free terminal edge 75 to provide a better seal.

In addition to the barrier leg cuffs 72, the article may comprise gasketing cuffs 76, which are joined to the chassis of the absorbent article, in particular to the topsheet 34 and/or the backsheet 36 and are placed externally relative to the barrier leg cuffs 72. The gasketing cuffs 76 may provide a better seal around the thighs of the wearer. A gasketing cuff may comprise a proximal edge 78 and a free terminal edge 77. The free terminal edge 77 may comprise a folded edge. Each gasketing cuff may comprise one or more elastic elements 60 in the chassis of the absorbent article between the topsheet 34 and backsheet 36 in the area of the leg openings. All, or a portion of, the barrier leg cuffs and/or gasketing cuffs may be treated with a lotion or another skin care composition. In further embodiments, the leg gasketing system comprises barrier leg cuffs that are integral with gasketing cuffs.

In certain embodiments, the leg gasketing system includes one or more printed substrates 15.

Elastic Waist Feature

Figure 3:
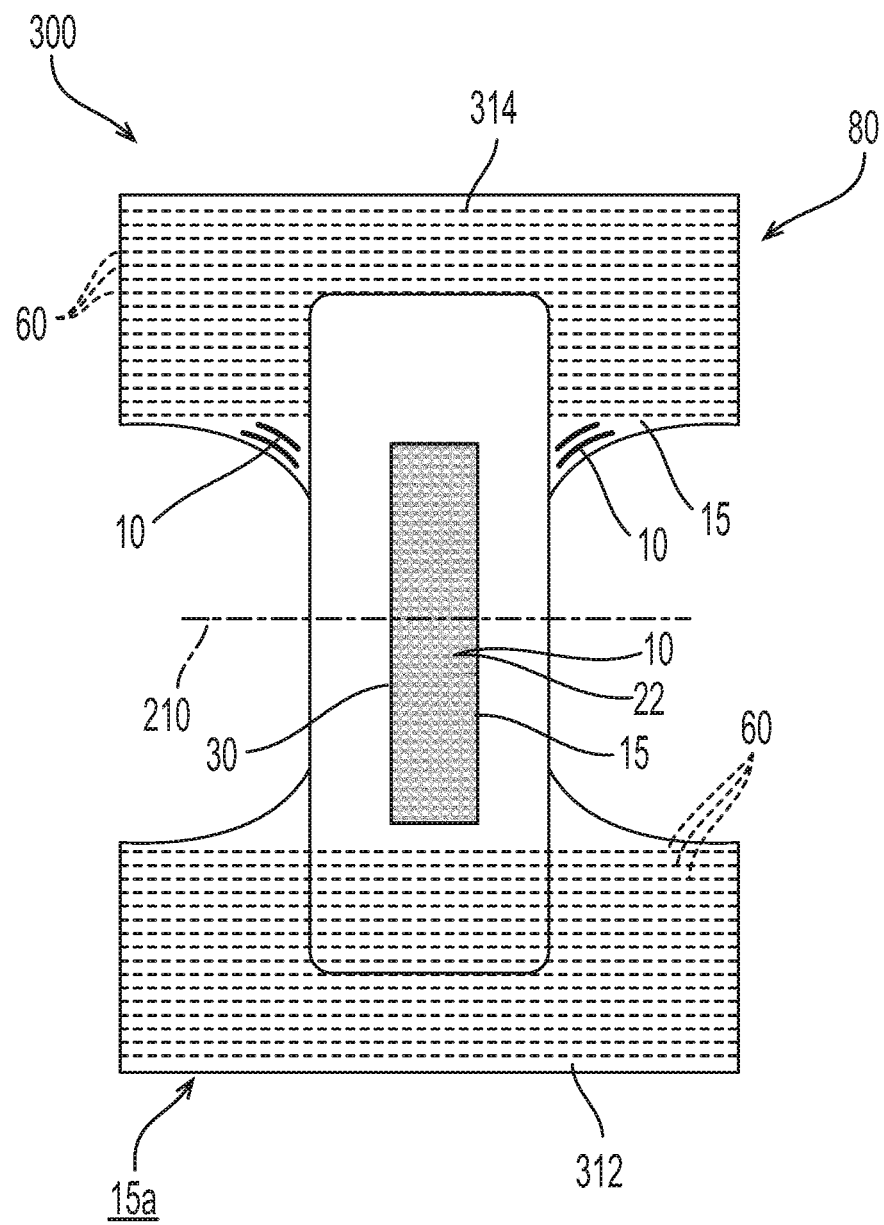
FIG. 3 is a schematic plan view of another exemplary embodiment of absorbent article. The absorbent article is shown in a flat, uncontracted state.
Figure 4:
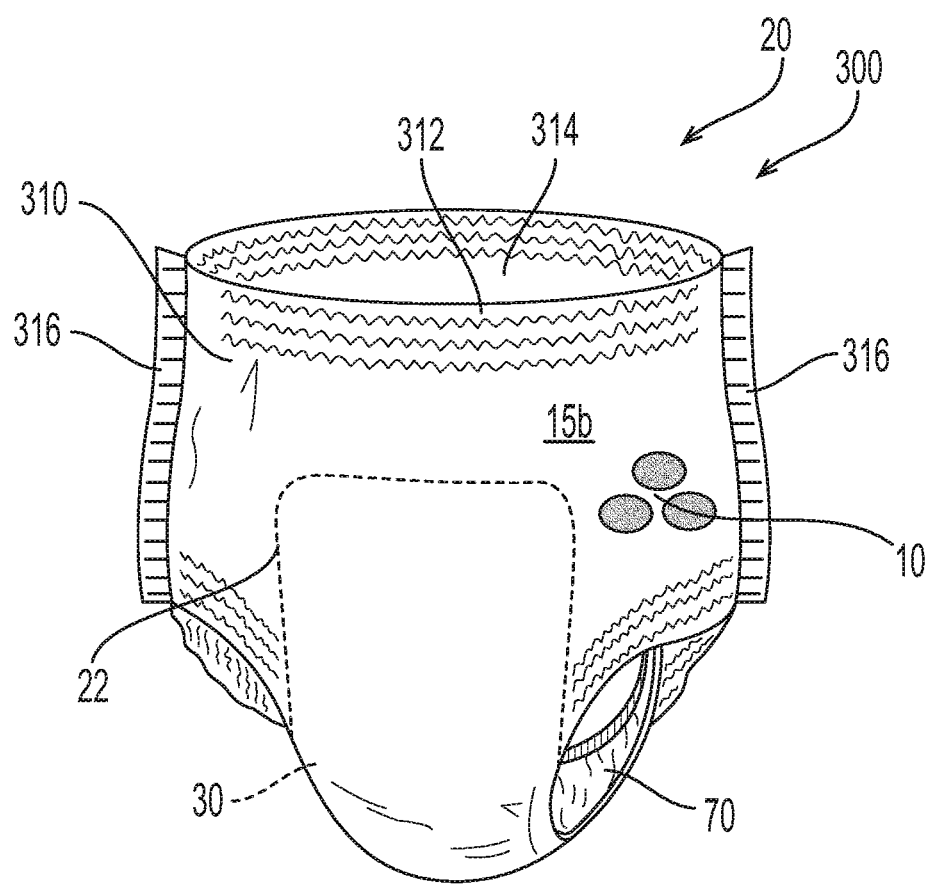
FIG. 4 is a schematic perspective view of another exemplary embodiment of absorbent article.

The absorbent article 20 may comprise at least one elastic waist feature 80 that helps to provide improved fit and containment, as shown in FIGS. 1 and 3-4. The elastic waist feature 80 is generally intended to expand and contract to dynamically fit the wearer's waist. Elasticized waist features include waistbands, waist cuffs having pockets 82 formed from a portion of the waist feature 80 that is unattached from the chassis 30, and waist panels designed to fit securely about the abdomen of the wearer. Nonlimiting examples of elasticized waist features are disclosed in U.S. patent application Ser. Nos. 13/490,543; 14/533,472; and 62/134,622. Waist features 80 may be joined to the chassis 30 in the first waist region 24 and/or in the second waist region 26. In nonlimiting examples, a waist feature 80 may comprise a printed substrate 15.

Pant Construction

In some embodiments, the article 20 may comprise an absorbent pant 300 as shown in FIGS. 3-4. The absorbent pant may comprise include a chassis 30, a belt 310 to be positioned about the wearer's waist, and optionally a leg gasketing system 70. FIG. 3 depicts an exemplary precursor structure of the pant in FIG. 4, in an open configuration laid out flat and stretched out laterally against elastic-induced contraction. In the final assembly of the pant, the front belt portion 312 is joined to rear belt portion 314 at seams 316, which may be permanent or refastenable side seams. Suitable refastenable seams are disclosed in U.S. Pat. Appl. Pub. No. 2014/0005020 and U.S. Pat. No. 9,421,137. Alternatively, instead of attaching belt 310 to the chassis 30 to form a pant, discrete side panels may be attached to side edges 22 of the chassis 30. The belt 310 and/or discrete side panels may be elastomeric. Exemplary belt and absorbent pant constructions are disclosed in U.S. patent application Ser. Nos. 14/598,783 and 14/032,595 U.S. Pat. Nos. 6,645,190; 8,747,379; 8,372,052; 8,361,048; 6,761,711; 6,817,994; 8,007,485; 7,862,550; 6,969,377; 7,497,851; 6,849,067; 6,893,426; 6,953,452; 6,840,928; 8,579,876; 7,682,349; 7,156,833; 7,201,744 and 7,901,393. Any suitable portion of a pant may include a printed substrate 15.

Test Methods

Migration Test Method

The Ink Migration test method disclosed herein can be used to quickly obtain qualitative ink formulation stability assessment and the ink formulation components' migration capability. The method comprises applying 3 drops of a filtered ink formulation using a disposable transfer pipette, onto a paper towel substrate. The ink is filtered through a syringe filter equipped with a Nylon filter having a pore size of 1.0 um and approximately 1-3 mL of filtered ink is collected in a suitable sized vial for later use. Suitable examples of paper towel substrates include Bounty® Basic paper towels, Bounty® Rinse and Re-Use paper towels, and Bounty® Select-A-Size paper towels, each available from Procter & Gamble, Cincinnati, Ohio. Multiple ink samples can be applied to the same paper towel substrate assuming that there is sufficient distance between the application points so as to not allow drops to spread over each other.

After applying the drops onto the paper towel substrate, the substrate is allowed to dry for 12-24 hrs at room temperature (approximately 68° F.-75° F.). The resulting ink drops will have spread across the substrate to a point where spreading/migrating is no longer observed. Inks exhibiting good formulation will show an even color distribution across the entire dispersed surface of the paper towel substrate. Inks exhibiting poor formulation will produce concentric rings of varying color intensity indicating that only certain components of the ink formulation migrated a first distance, while other components continued to migrate further. Without wishing to be bound by theory, it is believed that those inks containing components susceptible to migration or those inks having poor formulation stability will produce the spreading having concentric rings of varying color intensities, whilst those inks having fewer components susceptible to migration and those inks exhibiting good formulation stability will have a uniform color distribution across the entire spread ink.

The ink migration ratio is calculated by measuring the diameter, in millimeters, of the darkest, most intensely colored circle of the spread droplet, after drying, at is widest point. This distance, p, indicates the migration distance of the pigmented portion of the ink. If additional rings appear outside of this darkest ring, forming concentric circles, another measure is made of the diameter, in millimeters, of the subsequent ring or rings, and this value, t, represents the total furthest distance any component of the ink formulation was able to migrate. The ink migration value is determined by calculating the ratio of the furthest migrating component, t, to the least migrating component having the darkest color intensity, p. If only 1 complete, uniformly colored circle is observed, the migration ratio is deemed to equal 1.0.

Ink Rub-Off

Ink rub-off of a nonwoven substrate is performed on a Gakushin-type Rubbing Tester (a suitable instrument is a Model RT-300 available from Daiei Kagaku Seiki, Kyoto Japan or equivalent). The test specimen is mounted on the instrument and is rubbed against a standard abrading surface consisting of a receptor swatch (76.2 mm×25.4 mm, standard Crock Cloth Style #3, or equivalent) and a Standard Nonwoven (76.2 mm×25.4 mm, 13.5 gsm standard spunbond nonwoven, type 900-SB050, or equivalent) both available from Testfabrics Inc, West Piston, Pa. The Receptor Swatch is then measured using a spectrophotometer capable of making CIE L*a*b* measurements (a suitable instrument is the X-Rite eXact available from X-Rite, Grande Rapids, Mich. with 4 mm aperture, or equivalent) and the Ink Adhesion Rating (IAR) is calculated. All testing is performed at about 23° C.±2° C. and a relative humidity of about 50%±2%.

Specimens are tested using the following test fluids: a mineral oil having a Bp of 215° C.-643° C., flash point of 115° C. to 268° C., Density of 0.82 to 0.90 g/cm$^3$, and dynamic viscosity of 0.038 Pa·s at 38° C. (a suitable oil is RC-118 available from G-Biosciences, St. Louis, Mo. or equivalent) and a diaper rash cream containing zinc oxide and oil with a viscosity ≥10 Pa·s and shear rate of 10 sec$^{-1}$ at 25° C. Suitable diaper rash creams include HIPOGLOS® (available from Andromaco Laboratories of Buenos Aires, Argentina), DESITIN® Maximum Strength (manufactured by Johnson &Johnson of New Brunswick, N.J.), A+D® Diaper Rash Cream (manufactured by from Bayer AG of Germany) or equivalent.

All samples and test fluids are conditioned at about 23° C.±2° C. and a relative humidity of about 50%±2% for two hours prior to analysis. Remove a printed nonwoven specimen from the absorbent article, using freeze spray (such as Cyto-Freeze, Control Company, Houston Tex.) as necessary to remove the layer without distorting the dimensions of the nonwoven or damaging the printing. Visually locate the region on the sample with the highest print density. Cut a specimen 230 mm×25.4 mm of the nonwoven to be tested. In like fashion harvest 4 more test specimens from the equivalent position on four (4) additional replicate articles. Mount the five test specimens onto the movable, curved test stage with the printed sides facing away from the stage. The test specimens must be secured so that they do not move during testing. If a nonwoven specimen is not durable enough for rub testing (e.g. will stretch or tear), it is laminated onto a 300 mm by 25.4 mm sheet of copy paper with 2-sided tape before testing. In addition to the test specimens, a Control Nonwoven is also analyzed for comparison and calculation of $\Delta E_{CMC}$. The Control Nonwoven is compositionally identical to the specimen nonwoven with the exception that it has no printing within the 300 mm by 25.4 mm strip. If a non-printed area of the nonwoven is not available the Standard Nonwoven can be used as the Control Nonwoven.

For rub tests utilizing the mineral oil test fluid, place a Receptor Swatch on a bench and stack a Standard Nonwoven overlying it. Mount the stack on to the friction heads of the Rubbing Tester with the Standard Nonwoven facing outward and secure with the receptor clamp. Accurately pipet 0.25 mL of mineral oil onto the surface of the stack, allowing it to soak in. Lower the friction heads down onto the test specimen such that the Standard Nonwoven is in contact with the test specimens. Set the instrument to perform 15 cycles and start the test. Once complete, remove the Receptor Swatch and Standard Nonwoven from the friction, and discard the Standard Nonwoven. Allow the Receptor Swatch to condition for 24 hours at about 23° C.±2° C. and a relative humidity of about 50%±2% before evaluating.

For rub tests utilizing the diaper cream, place the Receptor Swatch onto the bench. Diaper Cream is applied in a specific pattern using a template. The template is a piece of plastic 76.2 mm by 25.4 mm by 0.60 mm thick into which 9 holes, each 6 mm in diameter, are drilled 3 to a row in a region approximately 20 mm by 20 mm square at the lateral and longitudinal center of the template. Place the template over the Receptor Swatch. Fill the holes flush with cream and remove the template. Stack the Standard Nonwoven on top of the Receptor Swatch. Mount the stack on to the friction heads of the Rubbing Tester with the Standard Nonwoven facing outward and secure with the receptor clamp. Lower the friction heads down onto the test specimen such that the Standard Nonwoven is in contact with the test specimens. Set the instrument to perform 15 cycles and start the test. Once complete, remove the Receptor Swatch and Standard Nonwoven from the friction head. Do not discard the Standard Nonwoven it will be analyzed as the Receptor Swatch/Standard Nonwoven stack. Allow the Receptor Swatch/Standard Nonwoven stack to condition for 24 hours at about 23° C.±2° C. and a relative humidity of about 50%±2% before evaluating.

Calibrate the spectrophotometer as per the manufacturer's instructions. Set the spectrophotometer to Abs white base, No Physical filter, illuminant C, 2° observer, ANSI T Density Standard. Place the Receptor Swatch onto the white ceramic plate (Available from Hunter Associates, with CIE L*a*b* values of approximately L*=93.6, a*=−1.3, b*=0.6). Visually divide the 20 mm×20 mm rub-off region into four quadrants. Measure L*a*b* centered at the most visually intense site within each quadrant, and then at the center of the rub-off region. Record values for the Control and each of the other specimens. Average the five readings for each and calculate the $\Delta E_{(CMC)}$ of the specimens verses the Control. Repeat for all mineral oil and diaper cream samples. Report as the arithmetic mean of $\Delta E_{cmc}$ of the 5 replicates to the nearest 0.01, separately for both mineral oil and diaper cream. Calculate and report Ink Adhesion Rating (IAR) for each of the test fluids using the following equation:

$$IAR = 5.04\left(1 + 0.47\left(\frac{\Delta E_{CMC}}{14.70}\right)\right)^{-\frac{1}{0.47}}.$$

Method for Measuring Color Density

Print color and density on a printed nonwoven or film is measured using a hand held, 45°/0° configuration, hemispherical geometry spectrophotometer, the X-rite eXact Spectrophotometer (available from X-Rite, Grand Rapids Mich.), or equivalent instrument, with a 4.0 mm optical aperture. This instrument measures print density based on reflection density expressed as the logarithm of the reciprocal of the reflectance factor. Set the scale to L*a*b* units, 2° Observer, C Illumination, Abs White Base, no Physical Filter, and the Density Standard of ANSI T. Measurements are performed in an environment controlled lab held at about 23° C.±2° C. and 50%±2% relative humidity.

Calibrate the instrument per the vendor's instructions using the standard white board (available as PG2000 from Sun Chemical-Vivitek Division, Charlotte, N.C.) (or alternatively a white ceramic plate (Available from Hunter Associates, CIELab values of approximately L*=93.6, a*=− 1.3, b*=0.6)) each day before analyses are performed. Remove the substrate to be measured from the sample article. If necessary, a cryogenic freeze-spray (e.g., Cytofreeze, available from Control Company, Houston Tex.) can be used to facilitate removal. Samples are conditioned at about 23° C.±2° C. and 50%±2% relative humidity for 2 hours before testing.

Place the Standard White Board on a horizontal bench, standard side facing upward. Place the specimen flat on top of the Standard White Board with the printed side facing upward. Place the eXact spectrophotometer on the specimen such that the measurement site is free of folds and wrinkles and 100% of the measurement site is within the instrument's aperture. Take a reading for density and L*a*b* color and record each to the nearest 0.01 units.

In like fashion the measure is repeated on corresponding sites on five (5) substantially similar printed substrates and the density and L*a*b* color values averaged separately and reported to the nearest 0.01 units.

EXAMPLES

The following tables show exemplary formulations of low migration ink compositions and characteristics thereof.

TABLE 1

Exemplary Low Migration Ink Compositions

| | Low Migration Ink Compositions | | | |
|---|---|---|---|---|
| Material | A | B | C | D |
| Mono-functional Acrylate Monomer | 34.9 | 43.0 | 30.8 | 30.8 |
| Di-functional Acrylate Monomer | 19.1 | 15.1 | 27.0 | 15.2 |
| Tri-functional Acrylate Monomer | 10.4 | 6.5 | 6.5 | 18.3 |
| Acrylate Oligomer | 8.7 | 8.7 | 8.7 | 8.7 |
| Photoinitiators | 11.7 | 11.7 | 11.7 | 11.7 |
| Pigment Dispersion | 12.3 | 12.3 | 12.3 | 12.3 |
| Additives, etc. to 100% | 2.9 | 2.7 | 3.0 | 3.0 |
| Ink Surface Tension (mN/cm²) | 39.1 | 40.5 | 38.6 | 38.3 |
| Ink Viscosity (cps.) | 25.3 | 19.7 | 24.3 | 27.7 |

TABLE 2

Low Migration Ink Compositions From Table 1

| | Low Migration Ink Compositions | | | |
|---|---|---|---|---|
| | A | B | C | D |
| IAR - Ink Adhesion rating | 2.8 | 3.4 | 3.4 | 2.9 |
| Optical Density | 0.27 | 0.44 | 0.27 | 0.27 |
| Functional Ratio (Mono- + Di-functional acrylate)/Tri-functional acrylates | 5.2 | 9.0 | 8.9 | 2.5 |
| Ink Migration Rating | 1.15 | 1.04 | 1.07 | 1.15 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A energy curable ink composition comprising, based upon total composition weight:
   a) from about 10% to about 80% of a solvent system comprising the following:
      i) from about 35% to about 80% of one or more mono-functional acrylate monomers;
      ii) from about 10% to about 35% of one or more di-functional acrylate monomers; and
      iii) from about 10% to about 30% of one or more tri-functional or greater acrylate monomers;
   b) from about 3% to about 30% of an acrylate oligomer; and
   c) from about 1% to about 15% of a colorant and
   wherein the composition is void of photoinitiators.

2. The energy curable ink composition of claim 1 further comprising, based upon total composition weight, of from about 0.5% to about 5% of one or more additives.

3. The energy curable ink composition of claim 2 wherein the one or more additives is selected from the group consisting of antioxidants, stabilizers, anti-misting agents, optical brighteners, surfactants, slip agents, waxes, silicones, defoamers, flow agents and leveling agents, solvents, amine curing synergists, gloss enhancers, rheology modifiers and combinations thereof.

4. The energy curable ink composition of claim 1 wherein the one or more mono-functional acrylate monomers are selected from the group consisting of lauryl acrylate, 2(2-ethoxyethoxy)ethyl acrylate, 2-phenoxyethyl acrylate, isobornyl acrylate, isodecyl methacrylate, tetrahydrofufuryl acrylate, dimethylaminoethyl methacrylate, and combinations thereof.

5. The energy curable ink composition of claim 1 wherein the one or more di-functional acrylate monomers are selected from the group consisting of dipropylene glycol diacrylate, tripropylene glycol diacrylate, ethoxylated hexanediol diacrylate, propoxylated hexanediol diacrylate, and combinations thereof.

6. The energy curable ink composition of claim 1 wherein the one or more tri-functional acrylate monomers are selected from the group consisting of trimethylol propane triacrylate, alkoxylated trimethylolpropane triacrylate, trimethylol propane trimethacrylate, alkoxylated glyceryl triacrylate, and combinations thereof.

7. The energy curable ink composition of claim 1 comprising a Functional Ratio of from about 2 to about 7.

8. The energy curable ink composition of claim 1 wherein the acrylate oligomer comprises at least two functional groups.

9. The energy curable ink composition of claim 1 wherein the acrylate oligomer has a glass transition temperature of less than 50° C.

10. The energy curable ink composition of claim 1 wherein the colorant is selected from those having the following Color Index classifications: Green PG 7and 36; Orange PO 5, 16, 34, 36, 38, 43, 51, 60, 62, 64, 66, 67 and 73; Red PR 101, 112, 122, 146, 149, 170, 176, 178, 179, 181, 185, 187, 188, 200, 202, 207, 208, 214, 220, 224, 242, 251, 254, 255, 260, 264, 48:1, 48:2, 48:3, 52, 52:1, and 57:1; MagentaNiolet PV 19, 23, 31, and 37; Yellow PY 12, 13, 14, 17, 74, 83, 120, 138, 139, 155, 151, 168, 175, 179, 180, 181 and 185; Blue PB 15, 15:1, 15:2, 15:3, 15:4, 15:6; Black PB 2, 5 and 7; carbon black; titanium dioxide; zinc sulfide, and combinations thereof.

11. The energy curable ink composition of claim 1 wherein the colorant comprises a pigment that is in the form of a dispersion and has an average particle size of from about 1000 nm or less.

12. The energy curable ink composition of claim 1 wherein the composition has a surface tension of about 15 dyne/cm$^2$ to about 40 dyne/cm$^2$, and a viscosity at 25° C. of about 5 cps to about 40 cps.

13. The energy curable ink composition of claim 1 wherein the energy curable ink composition has a Migration Rating of 1.1 or less.

14. A substrate comprising the energy curable ink composition of claim 1 wherein the substrate comprises an ink adhesion rating of 2 or greater.

15. The substrate of claim 14 wherein the substrate comprises a nonwoven, a film or combinations thereof.

16. An absorbent article comprising a topsheet, a backsheet and an absorbent core disposed between the topsheet and the backsheet, wherein the backsheet comprises a substrate printed with an energy curable ink composition of claim 1.

17. The absorbent article of claim 16 wherein the printed substrate comprises an ink adhesion rating of 2 or greater.

* * * * *